(12) United States Patent
Katzman et al.

(10) Patent No.: US 10,468,133 B2
(45) Date of Patent: Nov. 5, 2019

(54) ARRANGEMENTS FOR INTRAORAL SCANNING

(71) Applicant: SmileDirectClub LLC, Nashville, TN (US)

(72) Inventors: Jordan Katzman, Nashville, TN (US); Alex Fenkell, Nashville, TN (US); David Katzman, Nashville, TN (US); Christopher Yancey, Nashville, TN (US); Josh Chapman, Nashville, TN (US); Jessica Cicurel, Nashville, TN (US)

(73) Assignee: SmileDirectClub LLC, Nashville, TN (US)

( * ) Notice: Subject to any disclaimer, the term of this patent is extended or adjusted under 35 U.S.C. 154(b) by 0 days.

(21) Appl. No.: 16/397,843

(22) Filed: Apr. 29, 2019

(65) Prior Publication Data

US 2019/0252068 A1    Aug. 15, 2019

Related U.S. Application Data (63) Continuation of application No. 16/130,762, filed on Sep. 13, 2018, which is a continuation-in-part of application No. 15/725,430, filed on Oct. 5, 2017.
(Continued)

(51) Int. Cl.
*G16H 40/20* (2018.01)
*A61C 7/08* (2006.01)
(Continued)

(52) U.S. Cl.
CPC ............ *G16H 40/20* (2018.01); *A61C 7/002* (2013.01); *A61C 7/08* (2013.01); *G06Q 10/02* (2013.01);
(Continued)

(58) Field of Classification Search
CPC ........ G16H 40/20; G16H 10/60; A61C 7/002; A61C 7/08; A61C 9/0053; G06Q 10/02;
(Continued)

(56) References Cited

U.S. PATENT DOCUMENTS 4,003,132 A    1/1977 Beck
4,763,791 A    8/1988 Halverson et al.
(Continued)

OTHER PUBLICATIONS

"203221—SmileCareClub" video, uploaded to YouTube on Jun. 10, 2014, https://www.youtube.com/watch?v=B43vT_1GnR0.
(Continued)

*Primary Examiner* — Elaine Gort
*Assistant Examiner* — Amanda R. Covington
(74) *Attorney, Agent, or Firm* — Foley & Lardner LLP (57) ABSTRACT

Systems and methods include determining, by an appointment management system, a condition that an appointment to conduct an intraoral scan at an intraoral scanning site has been missed by a user, automatically generating a message to the user based on the condition that indicates that an at-home impression kit will be sent to the user, sending the automatically generated message to the user, sending the at-home impression kit to the user, receiving the at-home impression kit from the user, and producing, at a fabrication site, a plurality of aligners based on the received at-home impression kit where the plurality of aligners are specific to the user and are configured to reposition one or more teeth of the user in accordance with a treatment plan.

19 Claims, 7 Drawing Sheets

Related U.S. Application Data (60) Provisional application No. 62/660,141, filed on Apr. 19, 2018, provisional application No. 62/522,847, filed on Jun. 21, 2017.

(51) Int. Cl.
*G06Q 10/02* (2012.01)
*A61C 7/00* (2006.01)
*G16H 10/60* (2018.01)
*G06Q 10/10* (2012.01)
*A61C 9/00* (2006.01)
*A61B 6/14* (2006.01)

(52) U.S. Cl.
CPC ......... *G06Q 10/1095* (2013.01); *G16H 10/60* (2018.01); *A61B 6/145* (2013.01); *A61C 9/0053* (2013.01)

(58) Field of Classification Search
CPC .... G06Q 10/1095; G06Q 50/22; G06Q 50/24; A61B 6/145; G06F 19/30; G06F 19/32; G06F 19/34
See application file for complete search history.

(56) References Cited

U.S. PATENT DOCUMENTS

| | | |
|---|---|---|
| 5,190,168 A | 3/1993 | French et al. |
| 5,385,155 A | 1/1995 | Kittelsen et al. |
| 5,882,192 A | 3/1999 | Bergersen |
| 6,582,225 B1 | 6/2003 | Bergersen |
| 7,597,245 B1 | 10/2009 | Tillery |
| 7,967,145 B2 | 6/2011 | Tchouangang |
| 8,303,301 B2 | 11/2012 | Bergersen |
| 9,256,962 B2 | 2/2016 | Berry et al. |
| 9,715,753 B2 | 7/2017 | Berry et al. |
| 9,757,065 B1 | 9/2017 | Suri et al. |
| 2002/0143574 A1 | 10/2002 | Karras et al. |
| 2002/0188478 A1 | 12/2002 | Breeland et al. |
| 2003/0138752 A1 | 7/2003 | Bergersen |
| 2004/0091835 A1 | 5/2004 | Roetzer |
| 2004/0185415 A1 | 9/2004 | Ghim |
| 2005/0182654 A1 | 8/2005 | Abolfathi et al. |
| 2006/0057541 A1 | 3/2006 | Kahwaty |
| 2006/0064329 A1 | 3/2006 | Abolfathi et al. |
| 2006/0154198 A1 | 7/2006 | Durbin et al. |
| 2006/0173708 A1 | 8/2006 | Vining et al. |
| 2006/0275731 A1 | 12/2006 | Wen et al. |
| 2006/0275736 A1 | 12/2006 | Wen et al. |
| 2007/0061166 A1 | 3/2007 | Ramasubramanian et al. |
| 2007/0238065 A1 | 10/2007 | Sherwood et al. |
| 2008/0159798 A1 | 7/2008 | Culp et al. |
| 2008/0308450 A1 | 12/2008 | Tchouangang |
| 2009/0061381 A1 | 3/2009 | Durbin et al. |
| 2009/0081604 A1 | 3/2009 | Fisher |
| 2009/0081611 A1 | 3/2009 | Hines et al. |
| 2009/0136893 A1 | 5/2009 | Zegarelli |
| 2009/0215003 A1 | 8/2009 | Swain et al. |
| 2010/0036682 A1 | 2/2010 | Trosien et al. |
| 2010/0105011 A1 | 4/2010 | Karkar et al. |
| 2011/0084093 A1 | 4/2011 | Nehren et al. |
| 2011/0183293 A1 | 7/2011 | Tchouangang |
| 2012/0065985 A1 | 3/2012 | Royal et al. |
| 2012/0083549 A1 | 4/2012 | Kamohara et al. |
| 2012/0267811 A1 | 10/2012 | Weitzman |
| 2012/0330677 A1 | 12/2012 | Velimesis |
| 2013/0028617 A1 | 1/2013 | Fukuoka et al. |
| 2013/0035955 A1 | 2/2013 | Torres |
| 2013/0286174 A1 | 10/2013 | Urakabe |
| 2014/0379356 A1 | 12/2014 | Sachdeva et al. |
| 2015/0010879 A1 | 1/2015 | Kurthy |
| 2015/0257859 A1 | 9/2015 | Akl |
| 2016/0012182 A1 | 1/2016 | Golay |
| 2016/0034871 A1 | 2/2016 | Vargas et al. |
| 2016/0253464 A1* | 9/2016 | Balwani ................. G06Q 50/22 705/2 |
| 2016/0256240 A1 | 9/2016 | Shivapuja et al. |
| 2016/0263732 A1 | 9/2016 | Lourenco et al. |
| 2016/0317264 A1 | 11/2016 | Derraugh et al. |
| 2017/0010252 A1 | 1/2017 | Bearup et al. |
| 2017/0020642 A1 | 1/2017 | Mah |
| 2017/0039423 A1 | 2/2017 | Cork et al. |
| 2017/0046486 A1 | 2/2017 | Cunningham |
| 2017/0156830 A1 | 6/2017 | Wallace |
| 2017/0231721 A1 | 8/2017 | Akeel et al. |
| 2017/0239018 A1 | 8/2017 | Kim |
| 2018/0110589 A1 | 4/2018 | Gao |
| 2018/0125610 A1 | 5/2018 | Carrier et al. |
| 2018/0206940 A1* | 7/2018 | Kopelman ............. A61C 7/002 |
| 2018/0263731 A1 | 9/2018 | Pokotilov et al. |
| 2018/0263733 A1 | 9/2018 | Pokotilov et al. |
| 2018/0285801 A1 | 10/2018 | Alde et al. |

OTHER PUBLICATIONS

"Affordable Clear Braces—Smile Care Club" video, uploaded to YouTube on Mar. 30, 2015, https://www.youtube.com/watch?v=Qk-VhbH1RVM.

"Clear Braces . . . At Home??! Review—Before & After—Cost" video, uploaded to YouTube on Oct. 7, 2014, https://www.youtube.com/watch?v=9wrwhRTPjtk&t.

"Smile Care Club Unboxing, Review, Tutorial" video, uploaded to YouTube on May 1, 2015, https://www.youtube.com/watch?v=p7Y5fMRnJWE.

"Speak Out Game—Ellen Show with Khloe Kardashian and Kevin Hart", uploaded to You Tube on Oct. 11, 2016, https://www.youtube.com/watch?v=RDILAiBFRLY.

"Step 1! Working on my Smile . . . Smile Care Club" video, uploaded to YouTube on Jan. 4, 2015, https://www.youtube.com/watch?v=T_F3Xt4Og7w.

International Search Report and Written Opinion for International Application No. PCT/US2018/038459, dated Oct. 22, 2018, 13 pages.

Kravitz et al., "Teledentistry, Do-It-Yourself Orthodontics, and Remove Treatment Monitoring", JCO, Dec. 2016, 9 pages.

Smile Care Club, "Impression Kit", Jul. 21, 2014, available for retrieval at URL https://vimeo.com/wmvproductions/review/115725718/28854a7f49.

Smile Care Club, "Impressions—New Box", 2015,available for retrieval at URL https://vimeo.com/wmvproductions/review/137176701/d45be82d56.

Smile Care Club, "Impressions—Old Box", 2015,available for retrieval at URL https://vimeo.com/wmvproductions/review/137176599/0b8020929d.

Smile Care Club, "Impressions ReEdit", 2016,available for retrieval at URL https://vimeo.com/wmvproductions/review/168249998/0b75310374.

Smile Care Club, "Impressions", 2015,available for retrieval at URL https://vimeo.com/wmvproductions/review/136533463/1a8515abf5.

Smile Care Club, "Promo", 2014, available for retrieval at URL https://vimeo.com/wmvproductions/review/115725719/9c8235cdf2.

"Invisalign Manufacturing Process English" video, uploaded to YouTube on Apr. 7, 2014, https://www.youtube.com/watch?v=vsR0_wTR2a8.

"Smile Direct Club SmileShop Visit" video, uploaded to YouTube on Nov. 2, 2016, https://www.youtube.com/watch?v=wYQdNHPJb18.

International Search Report in International Patent Application PCT/US2018/065133 dated Apr. 22, 2019 (2 pages).

Smile Care Club, "Making Dental Impressions" video, Mar. 2016, 74 pages of screenshots.

Smiledirectclub, "What's a Smile Shop?", https://blog.smiledirectclub.com/what-is-smiledirectclub-smileshop/ Apr. 6, 2017, 7 pages.

* cited by examiner

[Form 402 with fields: NAME ON CREDIT CARD, BILLING ADDRESS, CITY, STATE, ZIP CODE, CREDIT CARD NUMBER, MM/YYYY, SECURITY CODE, E-MAIL ADDRESS]

Due to high demand, we ask that you provide your credit card information to hold your reservation. A refundable $25 hold will be placed on your credit card for holding your reservation. This hold will not be billed to you unless you do not show up for your appointment.

[HOLD MY RESERVATION] 404
[OPT OUT] 406

500

Your reservation has been reserved!

We will still hold your reservation!

Even though you didn't provide your credit card information, we will still hold your reservation – just for you!

Health and Consent Questionnaire

Yes / No — Do you have a bonded retainer?

Yes / No — Do you have crowns?

Yes / No — Do you have any bridgework?

Yes / No — Do you have an impacted tooth?

Yes / No — Do you have veneers?

Yes / No — Do you feel any pain in any of your teeth?

Yes / No — Do you authorize us to administer an intraoral scan?

ARRANGEMENTS FOR INTRAORAL SCANNING

CROSS-REFERENCE TO RELATED APPLICATIONS

This application is a continuation of U.S. patent application Ser. No. 16/130,762, filed Sep. 13, 2018, which claims the benefit of and priority to U.S. Provisional Patent Application No. 62/660,141, filed Apr. 19, 2018. U.S. patent application Ser. No. 16/130,762 is also a continuation-in-part of U.S. patent application Ser. No. 15/725,430, filed Oct. 5, 2017, which claims the benefit of and priority to U.S. Provisional Patent Application No. 62/522,847, filed Jun. 21, 2017. All of the aforementioned applications are incorporated herein by reference in their entirety.

TECHNICAL FIELD

The present disclosure relates generally to the field of intraoral scanning, and more specifically, to intraoral scanning for generating a three-dimensional image of a user's teeth that is used in treating misalignment of the user's teeth.

BACKGROUND

Dental impressions and associated physical or digital reproductions of a patient's teeth can be used by dentists or orthodontists to diagnose or treat an oral condition, such as the misalignment of the patient's teeth. For example, to take a dental impression, a dental tray having a viscous, thixotropic impression material is fit over the dental arches of the patient, and then the impression material sets to a solid over time, thereby providing an imprint of the patient's dental arches once the dental trays are removed from the patient's mouth. The impressions provide a detailed and stable negative of the patient's teeth and tissues in their mouth. The negative impressions may then be utilized to produce a physical or digital reproduction of the patient's teeth and surrounding tissues.

Traditionally, dental impressions are made in a dental office and require significant time. Dental offices typically deliver the dental impressions to an outside vendor that utilizes the impressions to form a positive model of the teeth and surrounding tissue. If the dental impressions includes any errors (e.g., incomplete impression of the teeth and tissues), the patient may be required to return to the dental office to have a second impression made. Furthermore, if the dental impressions are used by the dental professional in the course of administering a continuing treatment plan, the patient is typically required to undergo many check-up appointments at the dental office so that the dental professional can track the patient's treatment and modify the treatment plan as necessary. Each of these examples results in significant inconvenience to the patient and increases the cost of the treatment plan to both the dental professional and the patient.

SUMMARY

According to one aspect of the disclosure, a method of producing aligners for repositioning one or more teeth of a user is disclosed. The method includes receiving, by an appointment management system, a request to schedule an appointment at an intraoral scanning site having an intraoral scanner configured to conduct an intraoral scan of a mouth of a user. The method includes scheduling, by the appointment management system, the appointment in accordance with the request. The method includes generating and communicating, by the appointment management system, a message to the user. The message includes a confirmation confirming the scheduled appointment. The method includes conducting, using the intraoral scanner, the intraoral scan at the intraoral scanning site during the scheduled appointment. The intraoral scan generates three-dimensional data of the mouth of the user. The method includes generating, by a treatment plan computing system at a treatment plan site, a treatment plan for the user based on the three-dimensional data of the mouth of the user. The method includes receiving an approval of the treatment plan by a dental or orthodontic professional. The approval is received without the dental or orthodontic professional physically seeing the user in person. The method includes producing, at a fabrication site, a plurality of aligners based on the treatment plan. The plurality of aligners are specific to the user and are configured to reposition one or more teeth of the user in accordance with the treatment plan. The method includes sending the plurality of aligners to the user.

According to another aspect of the disclosure, a method of administering aligners for repositioning one or more teeth of a user is disclosed. The method includes requesting, via a web portal or mobile application, an appointment at an intraoral scanning site having an intraoral scanner configured to conduct an intraoral scan of a mouth of a user. The method includes receiving, from an appointment management system, a confirmation message confirming the scheduled appointment. The method includes receiving, via the intraoral scanner, the intraoral scan at the intraoral scanning site during the scheduled appointment. The intraoral scanner generates three-dimensional dimensional data of the mouth of the user. The method includes receiving a plurality of aligners which are generated in accordance with a treatment plan. The treatment plan is generated at a computing system by a dental or orthodontic professional without physically seeing the user. The treatment plan is generated based on the three-dimensional data of the mouth of the user. The plurality of aligners are specific to the user and configured to reposition one or more teeth of the user in accordance with the treatment plan. The method includes administering the plurality of aligners in a predetermined sequence to reposition the one or more teeth of the user in accordance with the treatment plan.

According to another aspect of the disclosure, a system for generating aligners for modifying an alignment of a user's teeth is disclosed. The system includes an appointment management system, an intraoral scanning site, and a fabrication site. The appointment management system is configured to receive a receive a request to schedule an appointment for receiving an intraoral scan of a mouth of a user. The appointment management system is further configured to schedule the appointment. The appointment management system is further configured to generate and communicate a message to a user device associated with the user. The message includes a confirmation confirming the scheduled appointment. The intraoral scanning site includes an intraoral scanner configured to generate three-dimensional data from an intraoral scan of the mouth of the user. The intraoral scanning site includes one or more computing systems configured to communicate the three-dimensional data from the intraoral scan for generation of a treatment plan. The fabrication site includes one or more computing systems configured to receive data corresponding to the treatment plan. The fabrication site includes thermoforming equipment configured to produce a plurality of aligners based on the treatment plan data. The plurality of aligners are specific to the user and are configured to reposition one or more teeth of the user in accordance with the treatment plan. The one or more aligners are sent to the user for repositioning the one or more teeth of the user.

Various other embodiments and aspects of the disclosure will become apparent based on the drawings and detailed description of the following disclosure.

DETAILED DESCRIPTION

The present disclosure is directed to systems and methods for conducting an intraoral scan of a user at a location. A user can request an appointment at an intraoral scanning site. For example, the user can request an appointment in advance of the requested appointment time (e.g., online, via a mobile application, via a telephone call) or the user can request an appointment at the time of requested appointment (e.g., a "walk in"). In requesting the appointment at the intraoral scanning site, the user can provide various information for reserving the appointment, such as a reason for making the appointment (e.g., misaligned teeth) or a dental condition of the patient (e.g., having crowns, an impacted tooth). The user can make the request online (e.g., via an internet scheduling website associated with the intraoral scanning site). When the appointment timeslot is held for the user, one or more scheduling alerts can be communicated to the user (e.g., confirmation notification, reminder notification, appointment modification query). Upon arriving at the appointment, the user can provide health history and consent information. The user can receive the intraoral scan, and upon confirmation from the user to purchase the aligners, one or more sets of aligners configured to modify the alignment of the user's teeth can be sent to the user.

The systems and methods described herein may have many benefits including, but not limited to, increasing user excitement about the alignment process, increasing the likelihood of a user showing up for their appointment, and increasing the likelihood of a user purchasing aligners at the intraoral scanning site, as will be discussed in greater detail below.

Figure 1:
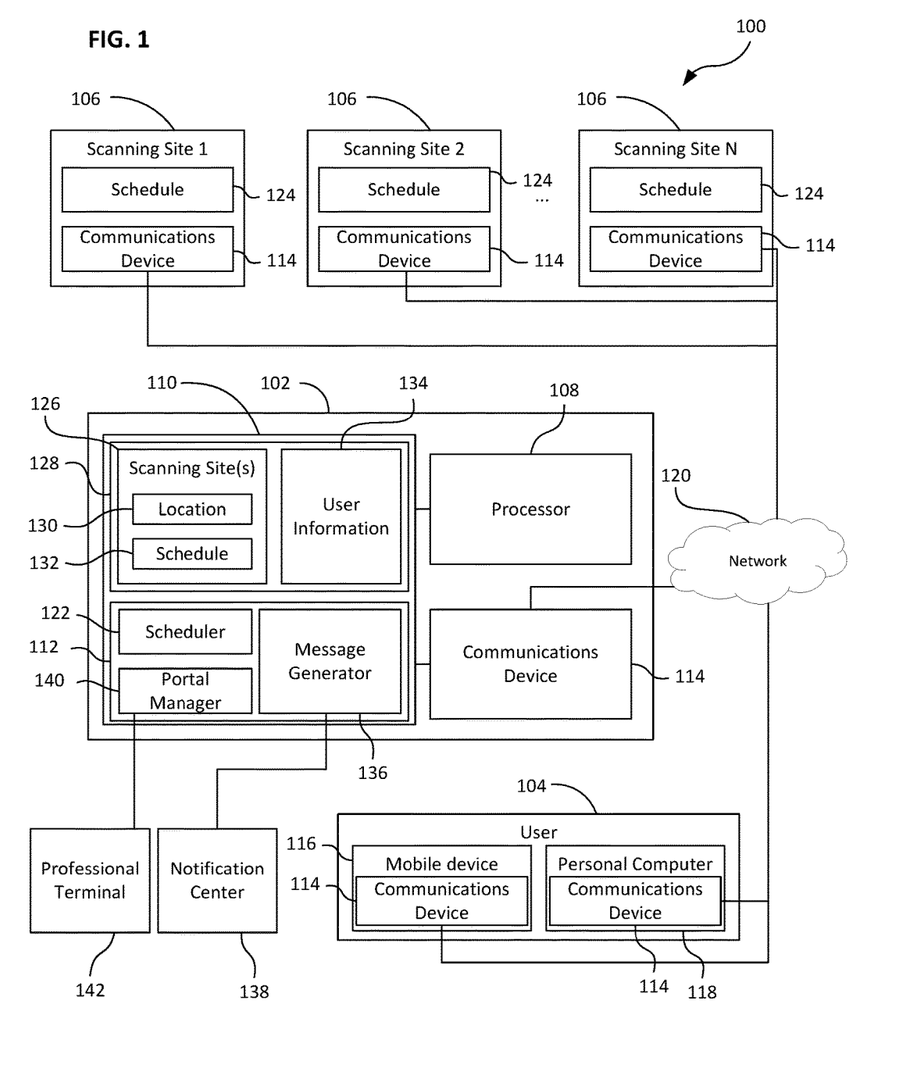
FIG. 1 shows an appointment management system according to an exemplary embodiment.

Referring to FIG. 1, an appointment management system 100 is shown. The appointment management system 100 includes a computing system 102, a mobile device 116 of a user 104, a personal computer 118 of the user 104, and a plurality of intraoral scanning sites 106.

The computing system 102 includes a processor 108 and memory 110. Processor 108 may be a general purpose or specific purpose processor, an application specific integrated circuit (ASIC), one or more field programmable gate arrays (FPGAs), a group of processing components, or other suitable processing components. Processor 108 may be configured to execute computer code or instructions stored in memory 110 or received from other computer readable media (e.g., CDROM, network storage, a remote server, etc.) to perform one or more of the processes described herein. Memory 110 may include one or more data storage devices (e.g., memory units, memory devices, computer-readable storage media, etc.) configured to store data, computer code, executable instructions, or other forms of computer-readable information. Memory 110 may include random access memory (RAM), read-only memory (ROM), hard drive storage, temporary storage, non-volatile memory, flash memory, optical memory, or any other suitable memory for storing software objects and/or computer instructions. Memory 110 may include database components, object code components, script components, or any other type of information structure for supporting the various activities and information structures described in the present disclosure. Memory 110 may be communicably connected to processor 108 via processing circuit 202 and may include computer code for executing (e.g., by processor 108, etc.) one or more of the processes described herein.

The memory 110 is described below as including various circuits 112. While the exemplary embodiment shown in the figures shows each of the circuits 112 as being separate from one another, it should be understood that, in various other embodiments, the memory 110 may include more, less, or altogether different circuits 112. For example, the structures and functions of one circuit 112 may be performed by another circuit 112, or the activities of two circuits 112 may be combined such that they are performed by only a signal circuit 112. Additionally, it should be understood that any of the functionalities described as being performed by a circuit 112 that is a part of the controller 112 may also be performed by a separate hardware component having its own processors, network interfaces, etc.

As shown in FIG. 1, the appointment management system 100 includes one or more communications device(s) 114. The communications device(s) 114 can be or include components configured to transmit and/or receive data from one or more remote sources. For instance, each of the intraoral scanning site(s) 106 may include a respective communications device 114, the user 104 may have one or more communications device(s) 114 embodied on the user's 104 mobile device 116, personal computer 118, etc., and/or the computing system 102 may include a communications device 114. Each of the respective communications devices 114 may permit or otherwise enable data to be exchanged between the user 104, the intraoral scanning site(s) 106, and/or the computing system 102. The communications device 114 may communicate via a network 120. The network 120 may be a Local Area Network (LAN), a Wide Area Network (WAN), a Wireless Local Area Network (WLAN), an Internet Area Network (IAN) or cloud-based network, etc. In some implementations, the communications device(s) 114 may access the network 120 to exchange data with various other communications device(s) 114 via cellular access, a modem, broadband, Wi-Fi, satellite access, etc.

Generating an Appointment

In some implementations, the user 104 may access a website (or other network-based portal) associated with the appointment management system 100. The user 104 may book an appointment at an intraoral scanning site 106 on the website. The user 104 may be directed to the website through, for instance, an advertisement on the user's 104 social media account. Additionally or alternatively, the user 104 may search for (e.g., on the internet, etc.) the website associated with the appointment management system 100.

Additionally or alternatively, the user 104 may receive a message directing them to the website to book an appointment at an intraoral scanning site 106. The processor 108 may control the communications device 114 to send the message to the user 104 in response to various conditions. For instance, the processor 108 may determine that the user 104 previously signed up to receive an in-home dental impression kit and never returned the completed kit. The processor 108 may identify a time between an order date (or shipment date) of the dental impression kit and the current date. The processor 108 may compare the identified time to a threshold time indicative of the user 104 likely not returning impressions from the dental impression kit. Where the identified time exceeds the threshold time, the processor 108 may automatically generate and send the message to the user 104. As another example, the processor 108 may determine that the impressions received from the user 104 were, for instance, incomplete. A technician may review the impressions (or a scan thereof) to determine their suitability for manufacturing dental aligners. When the impressions are determined to be incomplete, the technician may flag the impressions as incomplete. When the impressions are flagged, the processor 108 may automatically generate and send the message to the user 104 prompting the user to schedule an intraoral scan.

The website may include a home page, an instructional page detailing how the customer aligner process works, a results page, a locations page, and/or additional or alternative pages. Each of these pages may present different information to the user 104. For instance, the home page may present information pertaining to an overall user experience. The instructional page may present a step-by-step overview starting from an appointment to receiving customized aligners. Additionally, the instructional page may present a video to the user 104. The video may include graphics and/or text that show how the customized aligners reposition the user's 104 teeth, among other information. The video may also show the user 104 what to expect upon arrival at their appointment location, should they choose to book an appointment. The results page may include before-and-after pictures (or a rolling video of before-and-after pictures) of previous users who have used aligners to reposition their teeth. The locations page includes locations associated with each of the respective intraoral scanning sites 102.

Figure 2:
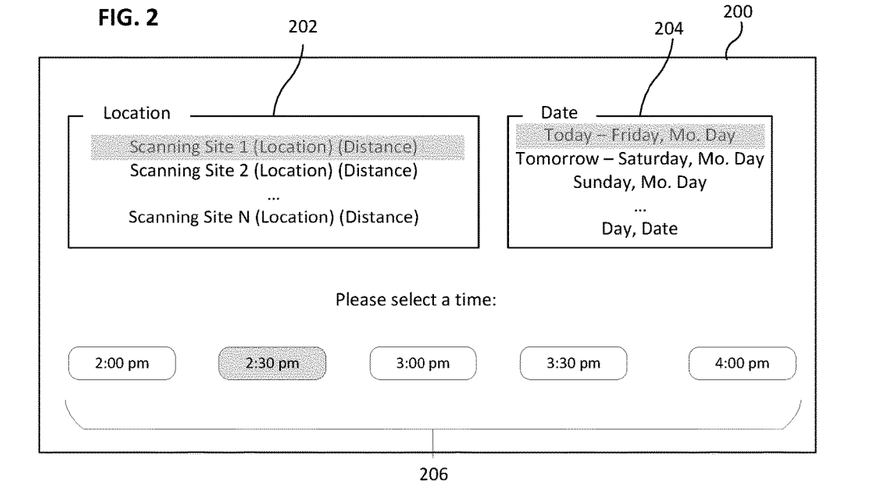
FIG. 2 shows a reservations screen associated with the appointment management system of FIG. 1 according to an exemplary embodiment.

Referring now to FIG. 1 and FIG. 2, the user 104 may access the locations page of the website. Specifically shown in FIG. 2 is a reservation page 200 which may be a portion of the locations page or a portion of the home page.

In some embodiments, the computing system 102 may include a scheduler 122. The scheduler can be or include instructions that, when executed by the processor 108, cause the processor 108 to generate and/or manipulate pages and displays for scheduling an appointment at an intraoral scanning site 106. While shown as embodied on memory 110 of the computing device 102, in some implementations, the scheduler 122 may be separate from the computing device 102. For instance, the scheduler 122 may be located remotely from the computing device 102. In instances such as these, the scheduler 122 may have a separate processor 108 and memory 110 (a dedicated processor and memory, for example). A user 104 may schedule an intraoral scan at a particular intraoral scanning site 106 via the website. The website may be controlled by the processor 108 using instructions from the scheduler 122. Following the intraoral scan, the user 104 may, in some instances, order aligners that are customized for the user 104. For instance, the user 104 may be satisfied with the overall process at the intraoral scanning site 106 and results of other users 104. Therefore, the user 104 may purchase aligners for aligning the user's 104 teeth. The aligners may be constructed of a polymer material, such as Polyethylenterephthalat-Glycol Copolyester (PET-G), which is thermoformed to positive molds (or models) of the user's 104 dentition at various intervals between a starting position and an ending position. The positive molds of the user's dentition 104 may be generated based on the treatment plan. The aligners may be used by the user 104 in stages to move the user's teeth towards the ending position. For example, the user 104 may be directed to wear a first aligner during a first month, a second aligner during a second month, a third aligner during a third month, and so on for a treatment period. These aligners may be shipped to the user 104 following production of the aligners (e.g., at a fabrication site which generates or otherwise produces the aligners). In some instances, the aligners may be shipped in stages, all at once in one box, etc. Each of the aligners may be administered by the user in a predetermined sequence and for a predetermined duration. For instance, a first aligner (which corresponds to a starting position of the user's teeth) may be administered by the user for a duration (e.g., a month, 90 days, etc.), a second (and additional intermediate) aligner(s) may be administered by the user for the same duration, and a final aligner may be administered for the same duration. Each of these aligners may move the user's teeth from the starting position to one or more intermediate positions, and from the one or more intermediate positions to the final positions based on the treatment plan.

As shown in FIG. 2, the reservation page 200 includes locations 202, dates 204, and times 206. Included in the locations 202 is information corresponding to each of the intraoral scanning site(s) 106. While each of the intraoral scanning site(s) 106 are shown as included, in some embodiments, only a subset of intraoral scanning site(s) 106 may be shown. For instance, the intraoral scanning site(s) 106 which are located nearest to the user 104 may be shown. As one example, the processor 108 may receive data from a communications device 114 associated with the user 104 (e.g., the mobile device 114, personal computer 118, etc.). The data may include location-based data associated with the user 104. The processor 108 may use this data to select, from each of the intraoral scanning site(s) 106, a subset of intraoral scanning site(s) 106 to include in the locations 202. As another example, the user 104 may be prompted to provide a zip code. The processor 108 may use the zip code provided by the user 104 to determine intraoral scanning site(s) 106 that are located nearest to (or within) the zip code.

In some implementations, a user 104 may search for specific locations 202 (instead of selecting ones that are nearest to the user's 104 location). The user 104, for instance, may be traveling to a different city than their city of residence and may want to schedule an appointment at an intraoral scanning site 106 located in that different city. As a result, the user 104 is not limited to scheduling appointments at intraoral scanning sites 106 in their own city, but may schedule appointments at any of the intraoral scanning sites 106. In implementations such as these, the user 104 may provide a zip code that is different from their current zip code (e.g., the zip code associated with the city to which they are traveling).

In still other implementations, one or more of the intraoral scanning sites 106 may be a mobile intraoral scanning site 106. For instance, the mobile intraoral scanning site 106 may be implemented in a vehicle (e.g., an automobile, a truck, a van, a bus, etc.), as part of a kiosk (e.g., located within another store or within a shopping mall), or comprise a pop-up location in operation for only a limited time period (e.g., one day, one week, one month). The mobile intraoral scanning site 106 may be included in the locations 202 on the reservations page 200. As will be described in further detail below, a user 104 may be able to arrange for the mobile intraoral scanning site 106 to travel to a set location (e.g., a location set by the user, such as their home or place of business), and the user 104 may receive an intraoral scan at the set location.

Upon selecting a location 202 of an intraoral scanning site 106 from the list of locations 202 of intraoral scanning sites 106, the user 104 may select an available date from the list of dates 204. Each intraoral scanning site 106 may maintain a schedule 124. The schedule 124 may be maintained locally (e.g., at each respective intraoral scanning site 106, etc.) and communicated to the computing system 102. The scheduler 122 can include instructions to access the schedule 124 of the intraoral scanning site 106 selected by the user 104 and determine available days/times for an appointment for the user 105 based on the schedule 124 for the intraoral scanning site. The scheduler 122 can include instructions to display available times and dates for the intraoral scanning site 106 based on the schedule 124 associated with the intraoral scanning site 106. Additionally or alternatively, the schedule 124 may be a cloud-based schedule that is remotely accessible by the processor 108 and by the respective intraoral scanning site 106. In implementations such as these, the memory 110 may store intraoral scanning site data 126 corresponding to each respective intraoral scanning site 106. The intraoral scanning site data 126 may be stored in a database 128 within memory 110. The intraoral scanning site data 126 may include a location 130 associated with the intraoral scanning site 106 (or other information usable to identify a particular intraoral scanning site 106) and a corresponding schedule 132 for the intraoral scanning site 106. The scheduler 122 can include instructions to determine the schedule for the selected location 202 of the intraoral scanning site 106 by cross-referencing data for the selected location 202 with location 130 within the intraoral scanning site data 126. Following cross-referencing the data for the selected location 202, the scheduler 122 can include instructions to identify the schedule for the corresponding selected location 202.

In each of these arrangements, the scheduler 122 can include instructions to identify available appointment times for the intraoral scanning site 106. These available appointment times may be presented to the user 104 for selection and booking an appointment.

As shown in FIG. 2, the intraoral scanning site(s) 106 may have extended hours (e.g., open nights, weekends, etc.). In implementations such as these, the user 104 may be more likely to schedule an appointment when the hours are extended due to a lessened likelihood of a scheduling conflict between the user 104 and a given intraoral scanning site 106.

The processor 108 may access the schedule 124, 132 for the selected location 202 to determine available dates via the instructions from the scheduler 122. The processor 108 may display the available dates in the list of dates 204. Following a selection of an available date from the list of dates 204, the times available for the selected date may be displayed to the user 104. The processor 108 may determine the available times in the same manner in which the available dates are determined. The user may select an available time to book their scan from the list of available times 206.

While described herein as the user first selecting a location, in some embodiments, the user may first select a preferred date and/or time and available locations (and/or dates and locations) may then be displayed based on the selected preferred date and/or time (and/or dates and locations). In each of these implementations, the user 104 may reserve a time at a particular intraoral scanning site 106, and at the reserved time, the user 104 may arrive at the particular intraoral scanning site 106 and receive their intraoral scan, as will be discussed in further detail below.

In some implementations, the user 104 may select the mobile intraoral scanning site 106. In implementations such as these, the processor 108 may identify a schedule 124, 132 associated with the mobile intraoral scanning site 106 using instructions from the scheduler 122. The user 104 may request a date 204 and time 206 that is available for the mobile intraoral scanning site 106. The user 104 may then provide a location to arrange the appointment with the mobile intraoral scanning site 106. The mobile intraoral scanning site 106 may have a predetermined radius (e.g., 10 miles, 20 miles, 25 miles, 50 miles, etc.) within which the mobile intraoral scanning site 106 operates. The user 104 may provide a location within the predetermined radius. At the reserved time, the mobile intraoral scanning site 106 may be driven to the location provided by the user 104. The user 104 may similarly arrive at the provided location at the reserved time and receive an intraoral scan, as will be discussed in further detail below.

Figure 3:
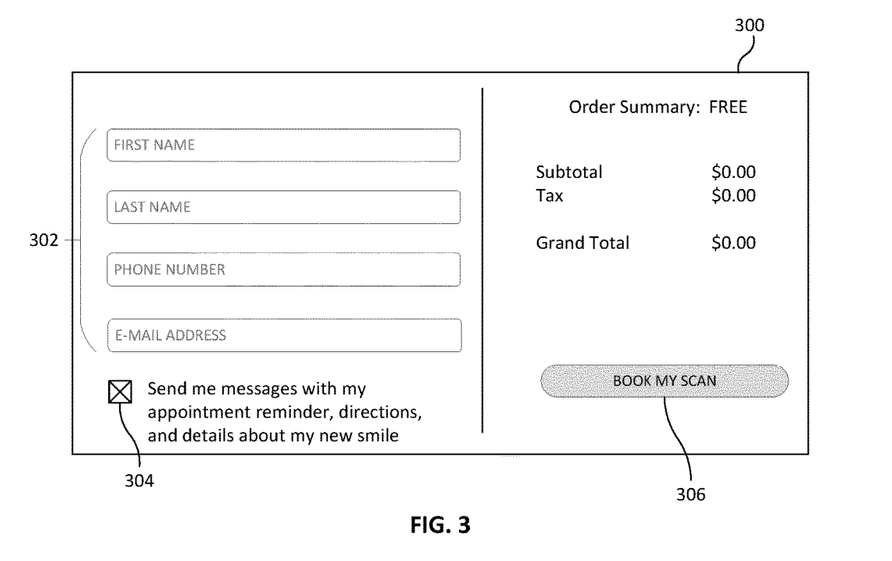
FIG. 3 shows a booking screen associated with the appointment management system of FIG. 1 according to an exemplary embodiment.

Referring now to FIG. 3, following the user 104 selecting an available time 206 (e.g., as shown in FIG. 2), the scheduler 122 can include instructions to direct the user 104 to a booking screen 300. At the booking screen 300, the user 104 may be prompted to provide various personal information 302 (e.g., first and last name, a phone number, an e-mail address, etc.). Additionally, the user 104 may be prompted to opt into (or not opt into) a messaging service by selecting box 304. The messaging service may provide one or more messages to the user 104 concerning the user's 104 booked appointment, as will be discussed in further detail below. The personal information 302 and data corresponding to whether the user 102 opted into the messaging service may be stored in database 128 in a user file 134. The user file 134 may be a file associated with the user 104 and may include various types of data associated with the user 104. The user file 134 may be subsequently used for generating messages to the user 104 before and/or after the user's 104 appointment. The user file 134 may also include the intraoral scan, the treatment plan, progress information, photographs, etc.

As shown in FIG. 3, the appointment may be free to the user 104. In some implementations, the appointment may have a flat fee (e.g., $25, $95, etc.). In still other implementations, the appointment may have a booking hold which is not charged to the user 104. Following the user 104 providing their personal information, the user 104 may be prompted to book their scan by selecting button 306.

Figure 4:
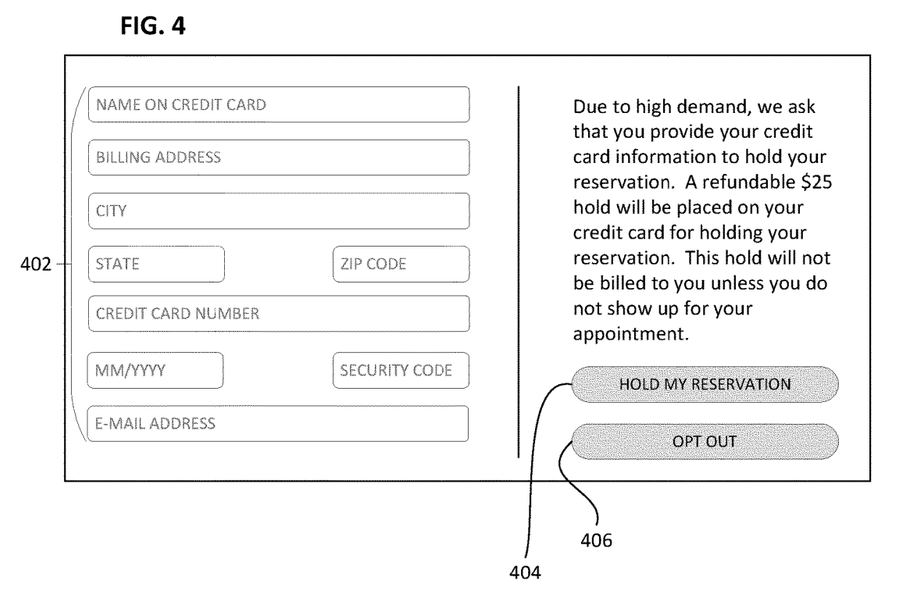
FIG. 4 shows a reservation hold screen associated with the appointment management system of FIG. 1 according to an exemplary embodiment.

Referring now to FIG. 4, when the user 104 books their scan by selecting button 306 (of FIG. 3), the scheduler 122 can include instruction to direct the user 104 to a holding page 400. At the holding page 400, the user 104 may be prompted to provide credit card information 402. The credit card information 402 may be requested to hold the available time selected by the user 104 (e.g., as selected on reservations page 200). The credit card information 402 may be used to place a hold (for instance, $25) on the user's 104 credit card. In some implementations, the hold may be a refundable hold (e.g., the credit card for the user 104 is not billed or is refunded unless the user 104 does not show up for their appointment at the selected time).

Figure 5A:
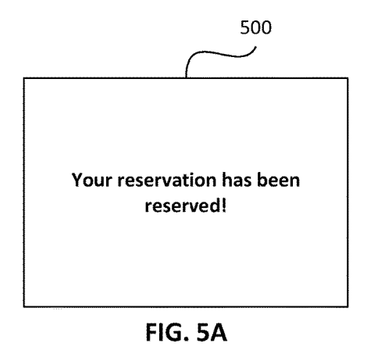
FIG. 5A and FIG. 5B show example confirmation windows associated with the appointment management system of FIG. 1 according to an exemplary embodiment.
Figure 5B:
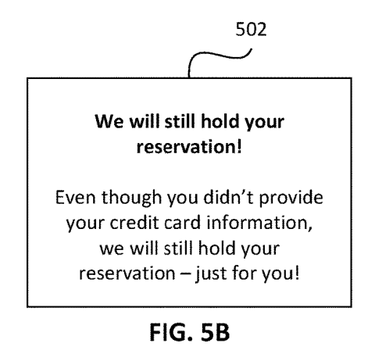

In some implementations, the hold may be optional. For instance, the user 104 may be able to hold the reservation (through selection of button 404) or opt out of holding the reservation (through selection of button 406). The user 104 may provide their credit card information 402 and select button 404. In selecting prompt 404, confirmation window 500 may be displayed to the user 104 (e.g., indicating that the user's 104 reservation has been confirmed). Additionally, the user 104 may not provide their credit card information 402, and instead, opt out by selecting button 406. In some implementations, selecting button 406 may direct the user 104 back to the reservations page 200. In other implementations, selecting button 406 may cause confirmation window 502 to be displayed to the user 104 (e.g., indicating that the user's 104 reservation is still confirmed despite the user 104 not providing credit card information 402). By providing credit card information 402, the user 104 may be more likely to show up for their appointment, despite their credit card never being charged.

In one or more embodiments, following the user 104 reserving (and optionally holding) their appointment, the user 104 may want to reschedule their appointment. To do so, the user 104 may call the intraoral scanning site 106 to reschedule their appointment. Additionally, the user 104 may go onto the website associated with the appointment management system 100, provide log-in information or other identifying information to look-up their appointment and access, for instance, a user portal (as will be discussed in greater detail below). The user portal may include various appointment-related information including the time, date, and location for their appointment. Following the user's appointment, the user portal may include various treatment plan information (such as a virtual representation of the user's 104 treatment plan at different stages or a simulated representation of the user's 104 teeth through progression of the treatment plan), progress information provided by the user 104, etc., as will be discussed in greater detail below. The user 104 may select their appointment and reschedule their appointment in substantially the same manner by which the user 104 booked their appointment (e.g., by following the progression from FIG. 2 through FIG. 4).

Pre-Appointment Messaging Services

Referring back to FIG. 1, when the user 104 opts into the messaging service (through selection of box 304 of FIG. 3), one or more messages may be automatically generated and communicated to the user 104 (e.g., via respective communications device(s) 114). For instance, the computing system 102 may include a message generator 136. The message generator 136 can be or include instructions that, when executed by processor 108, cause the processor 108 to generate a message to communicate to the user 104. The message generator 136 can include instructions to transmit the generated message to the user 104 via, for instance, the communications device 114 of the computing system 102 to the communications device 114 of the user's 104 mobile device 116 and/or personal computer 118. The message generator 136 can include instructions to identify a communications device 114 associated with the user 104 (e.g., by identifying the user file 134 associated with the user 104). The message generator 136 can include instructions to communicate the generated message to the user 104 upon one or more conditions, as will be discussed in further detail below. Accordingly, the various messages described herein may be communicated to the user's 104 mobile device 116 and/or the user's 104 personal computer 118. Various examples of messages will be discussed in turn below.

In some implementations, one or more messages that are generated via the message generator 136 may be communicated to a notification center 138. The notification center 138 may be, for instance, a call center. The messages that are communicated to the notification center 138 may be instructions to call a particular user 104 at a particular time to deliver a verbal message, as will be discussed in further detail below.

In some embodiments, the message generator 136 can include instructions for generating an appointment confirmation message. The message generator 136 can include instructions to determine when a user 104 has successfully reserved an appointment. The message generator 136 can include instructions to automatically communicate (e.g., via respective communications devices 114) the appointment confirmation message in response to the user 104 successfully reserving the appointment. The appointment confirmation message may be or include a message that indicates that the user's 104 appointment has successfully been reserved. In some implementations, the appointment confirmation message may include a link, which the user 104 may select, that causes the appointment to be automatically added to a calendar associated with the user 104. For instance, the appointment confirmation message may include a plurality of links associated with different types of calendar software. The user 104 may select the link corresponding to whichever type of calendar that is used by the user 104. Upon selecting the appropriate link, the appointment may automatically be added to the user's 104 calendar. The appointment added to the user's 104 calendar may include contact information associated with the corresponding intraoral scanning site 106, a location associated with the intraoral scanning site 106, time, and an expected duration of the appointment (e.g., 30 minutes).

In some embodiments, the message generator 136 can include instructions for generating one or more appointment reminder messages. The message generator 136 can include instructions to determine a current time and an appointment time (e.g., the time of the user's 104 appointment at the intraoral scanning site 106). The message generator 136 can include instructions to compare a time difference between the current time and appointment time to a threshold time. If the difference in time is less than (or equal to) the threshold time, the message generator can include instructions to automatically generate the appointment reminder message.

Figure 7:
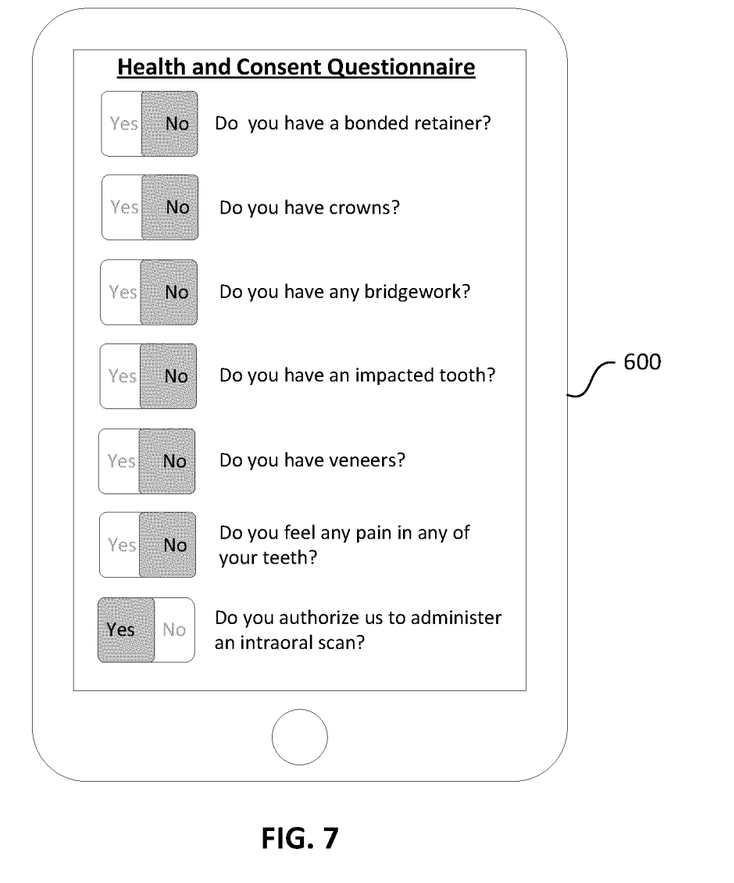
FIG. 7 shows a health and consent information screen displayed on a user device for enabling the user to provide health and consent information according to an exemplary embodiment.

In some implementations, the threshold time may be set based on a number of days (e.g., two days, three days, a week, etc.) until the user's 104 appointment. In implementations such as these, the appointment reminder message may be a message reminding the user 104 that they have an upcoming appointment. The appointment reminder message may be generated when the user 104 books an appointment well in advanced. Accordingly, where the user 104 books an appointment for a number of days in advanced that is less than a threshold number of days (e.g., two days, three days, a week, etc.), the appointment reminder message may not be generated. As one non-limiting example, the user 104 may book an appointment on a Monday. Where the user 104 books the appointment for the next Friday, the user 104 may be reminded of their appointment through generation of an appointment reminder message on the upcoming Wednesday. However, where the user 104 books the appointment for the next day (e.g., Tuesday), the user 104 may not receive an appointment reminder message. The appointment reminder message that is communicated to the user 104 may include various information including, for instance, directions to the intraoral scanning site 106, a phone number for the intraoral scanning site 106, etc. Additionally, the appointment reminder message may include various information pertaining to the user's 104 appointment. For example, the appointment reminder message may include a health and consent questionnaire for the user 104 to fill out. In some implementations, the health and consent questionnaire may have a plurality of Yes/No questions corresponding to various health-related conditions. The responses to the questions may be defaulted to "No", whereby the user 104 may only need to change those answers to the questions that do apply to the user 104. Referring briefly to FIG. 7, the user 104 may be shown several questions which are defaulted to "No". The user 104, however, may have an impacted tooth and an indicator on the health and consent questionnaire for an impacted tooth is defaulted to "No". Accordingly, the user 104 may maintain all defaulted answers except for the question relating to impacted teeth, which the user 104 may switch to answer "Yes." Such arrangements may expedite the overall process for the user's 104 experience at the intraoral scanning site 106. As another example, the appointment reminder may include before-and-after pictures for previous customers (e.g., similar to those described above with reference to the results page). Such arrangements may increase excitement and anticipation of the appointment for the user 104.

In some implementations, the threshold time may be set based on a location of the user 104 (e.g., as determined based on data provided by the user's 104 mobile device 116 and/or personal computer 118) with respect to the location of the intraoral scanning site 106. In implementations such as these, the appointment reminder message may be a message reminding the user 104 to leave for their appointment. The threshold may be determined based on factors in addition to the location of the user 104 including, for instance, a distance between the respective locations, traffic between the respective locations, weather, time of day, day of the week, etc. The appointment reminder message that is communicated to the user 104 may include various information including, for instance, directions to the intraoral scanning site 106, a phone number for the intraoral scanning site 106, etc.

In some implementations, the message generator 136 may include instructions to generate multiple appointment reminder messages. For instance, the message generator 136 may generate a first appointment reminder message to remind the user 104 that they have an upcoming appointment and a second appointment reminder message to indicate to the user 104 that they should leave for their appointment (e.g., now, in 15 minutes, in one hour, etc.).

In some embodiments, the message generator 136 can include instructions to identify specific users 104 for voice messages. For instance, where the user 104 does not provide credit card information 402 (thus opting out of reserving the appointment), such information may be stored in the user file 134. Where the user 104 does not provide credit card information 402, the message generator 136 can include instructions to generate a prompt for a voice message to communicate to the notification center 138. The prompt may instruct a person at the notification center to initiate a telephone call with the user 104, in which the user 104 will be informed about the overall process and experience at the intraoral scanning site 106, and the user 104 may provide one or more concerns regarding their smile. The call may be initiated by the person at the notification center a certain number of days prior to the user's 104 appointment (e.g., three days, five days, etc.). The person may annotate (or record) the conversation, and portions thereof may be saved to the user file 134. In embodiments such as these, the voice message may increase user 104 excitement for the appointment and increase the likelihood that the user 104 shows up for their scheduled appointment.

Appointment Management at an Intraoral Scanning Site

Figure 6:
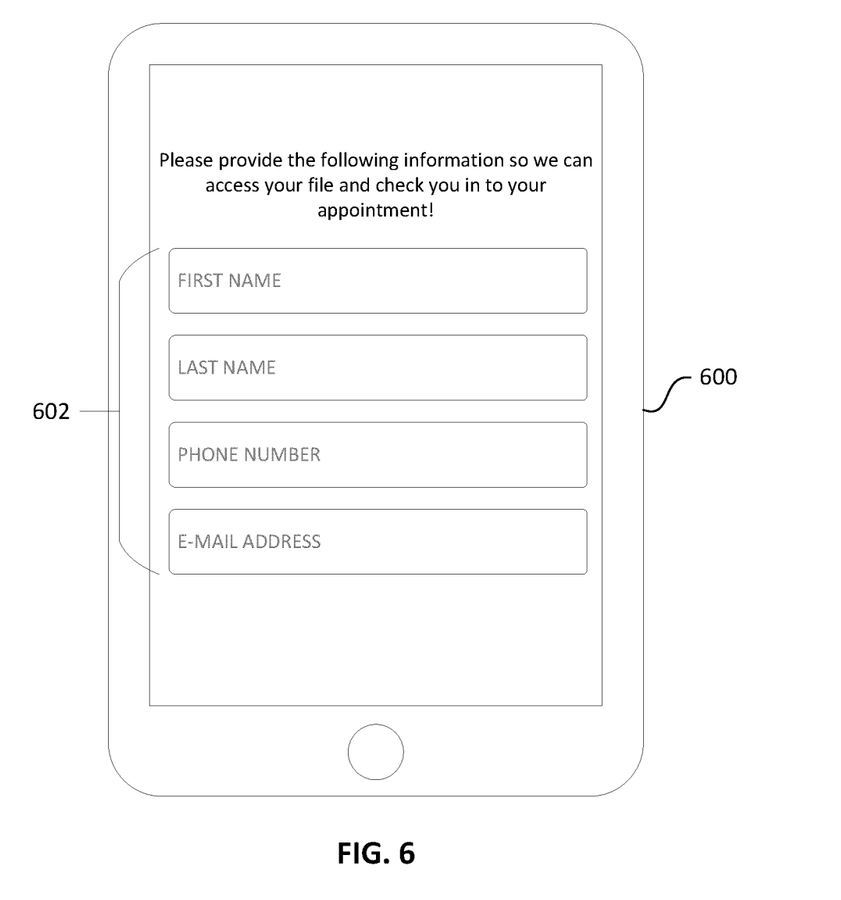
FIG. 6 shows a check-in screen displayed on a user device for enabling a user to check into an appointment according to an exemplary embodiment.

Referring now to FIG. 1 and FIG. 6, upon arrival at the intraoral scanning site 106, the user 104 may be presented with a user device 600. The user device 600 may be a tablet, for instance. The user 104 may be requested to provide personal information 602 (e.g., similar to the personal information 202) for accessing the user file 134. The processor 108 may retrieve the user file 134 associated with the user 104 and check the user 104 into their appointment. Where the user 104 does not show up within a predetermined timeframe (e.g., at the start time of their appointment, within five minutes after the start time, 10 minutes after their start time, etc.) the processor 108 may automatically indicate the user 104 did not show up for their scheduled appointment. The processor 108 may compare a time difference between the current time and the appointment start time to a predetermined timeframe. If the time difference exceeds the predetermined timeframe, the processor 108 may automatically indicate the user 104 did not show up for their scheduled appointment in the user file 134. Additionally or alternatively, a receptionist may indicate that the user 104 did not show up for their appointment in the user file 134. In some embodiments, the message generator 136 can include instructions for automatically generating a message to send to the user when the user is late for their appointment beyond a predetermined time frame (for instance, five minutes late). The message may ask the user to respond with whether they still plan on having an intraoral scan conducted, indicate that they do not need an appointment to receive their scan, prompt them to reschedule, etc.

In some instances, the intraoral scanning site 106 may include a screen (e.g., of a television or other display system) that displays before-and-after pictures of customers who previously used aligners. The before-and-after pictures may be similar to those described above with reference to the results page. The before-and-after pictures may be displayed on a rolling basis. In instances such as these, consumer confidence may be increased by observing historical results.

Referring now to FIG. 1 and FIG. 7, the user file 134 may include the health and consent questionnaire. Where the health and consent questionnaire was previously filled out by the user 104 (e.g., as it was received in an appointment reminder message), the health and consent questionnaire may be saved to the user file 134. However, where the health and consent questionnaire was not previously filled out by the user 104 (e.g., the user 104 never filled the questionnaire out or the questionnaire was never provided to the user 104), the user 104 may fill out the health and consent questionnaire via the user device 600. In some embodiments, where the user 104 switches an answer, a comment box is automatically generated and displayed to the user 104 prompting the user 104 to provide further details. For instance, where the user indicates that they are experiencing pain in their teeth, a comment box is automatically generated and displayed on the display of the user device 600. The user may provide an input, via the comment box, to elaborate on the pain in their teeth. While two examples of when the health and consent questionnaire are provided (e.g., following a reservation and following an appointment check-in but prior to the intraoral scan), the health and consent questionnaire may be provided to the user 104 to complete at any time throughout the scanning process after they arrive at the scanning location, such as during a break in procedures, following completion of the intraoral scan, etc. Accordingly, the present disclosure is not limited to any particular arrangement regarding when the health and consent questionnaire is completed by the user 104.

As shown in FIG. 7, the user device 600 may present the health and consent questionnaire to the user 104. As discussed above, the health and consent questionnaire may have a plurality of Yes/No questions corresponding to various health-related conditions. In some implementations, at least some of the questions for the health and consent questionnaire may be defaulted to a set response. For instance, the health-related questions for the questionnaire may be defaulted to "NO", whereas the consent-related questions for the questionnaire may be defaulted to "YES". In other instances, all of the questions may be defaulted to "NO". The user 104 can modify the responses to all the questions as needed. For instance, the user 104 may have bridgework and a question inquiring about whether the user 104 has bridgework is defaulted to "No". Accordingly, the user 104 may maintain the default answers to all the questions except for the question pertaining to bridgework. The user 104 may manually switch this answer to "Yes." In each of these implementations, the user's 104 experience at the intraoral scanning site 106 may be improved by expediting the health and consent questionnaire.

Following check-in and providing the responses to the health and consent questionnaire, the user 104 may be directed to a room where the user 104 will receive their intraoral scan. A technician at the scan shop 106 may administer the intraoral scan. The technician may administer the intraoral scan using, for instance, an iTero® scanner. As the technician administers the intraoral scan, the intraoral scanner may produce data which is visually represented on a display. The data may correspond to a three-dimensional scan of the user's 104 mouth. In some embodiments, the technician may administer the intraoral scan in a predetermined position. For instance, the technician may be instructed to administer the intraoral scan from over the user's 104 shoulder with the display in the field of view of the user 104. Accordingly, as the intraoral scanner generates data that is visually represented on the display, both the user 104 and technician may be able to observe the display. Such arrangements and instructions may enhance the user's 104 experience by engaging the user 104 in the scanning process.

In some embodiments, the administration of the intraoral scan may be recorded for quality assurance purposes. For instance, the room in which the user 104 has the intraoral scan administered may have a camera. The user 104 may approve or deny the recording. In some instances, the user 104 may be incentivized to approve the recording by, for instance, one free set of aligners or one free set of retainers.

In some embodiments, the user 104 may be shown a simulated movement of the user's teeth from the starting position (e.g., as represented by the three-dimensional scan) to a simulated final position. Such capabilities presently exist through use of the iTero® scanner.

Following administration of the intraoral scan, in some embodiments, a quality control technician may review and approve the intraoral scan. The quality control technician may be located at the intraoral scanning site 106. Additionally or alternatively, the quality control technician may be located remotely. The quality control technician may be a manager or other guide who has the authority to approve (or not approve) the intraoral scan. Where the quality control technician does not approve of the intraoral scan, the quality control technician may highlight particular areas on the intraoral scan that need to be re-scanned. The quality control technician may also approve some or all of the information provided by the user 104 (e.g., the personal information 202, the health and consent information provided in the health and consent questionnaire, various other information such as shipping information, etc.). In implementations such as these, the quality control technician may ensure that subsequent visits to the intraoral scanning site 106 or unnecessary calls to the user 104 are avoided by collecting all necessary information during a single appointment of the user 104.

In some embodiments, following administration of the intraoral scan, the technician may take one or more photographs of the user's 104 mouth. The technician may take the photographs of the user's 104 upper and lower jaw (in some instances with a smile spreader). The technician may take a head-on photograph of the user's 104 smile. The technician may take the one or more photographs using a digital camera. Additionally or alternatively, the technician may take the one or more photographs using a camera of the user device 600. In each of these implementations, the photographs may be an initial set of photos that is used for compliance checks. The photographs may be saved to the user file 134.

Once the quality control technician approves of the intraoral scan (and photographing), the user 104 may leave the room where the user 104 received their intraoral scan. The user may go to, for instance, a waiting area or front desk area. At the front desk area, the user 104 may be shown or given various products. For instance, the user 104 may be shown what the aligners generally look like (e.g., substantially transparent, translucent, etc.). The user 104 may also be shown the packaging in which the aligners are delivered and the corresponding instruction manual. The user 104 may be provided with various dental-related items. For instance, the user 104 may be provided with lip balm, teeth whitening kits, a tote bag, etc. Each of these examples may further increase the likelihood of the user 104 purchasing aligners that are custom to the user's 104 teeth. In some embodiments, instead of receiving products at a front desk area, the user 104 may be shown or given various products in the room where they received the intraoral scan. In some embodiments, the user 104 may be shown the aligners/packaging prior to receiving the intraoral scan (e.g., at check-in), during a break, etc.

In some embodiments, the user 104 may be presented with a fast track option for generating a set of aligners from the intraoral scan. The fast track option may be a form that is filled out by the user 104, may be an oral agreement from the user, etc. The fast track option may authorize a provider of the aligners to automatically generate the aligners once the treatment plan (or the final teeth position) for the user 104 is approved by a doctor (e.g., a dentist, an orthodontist, etc.).

The user 104 may be prompted to pay at the time of the intraoral scan (or set up a payment plan at the time of the intraoral scan). Once the user 104 pays (or sets up the payment plan), the user 104 may authorize fast tracking the generation of the aligners. In implementations such as these, the user 104 may not be required to authorize the treatment plan. Rather, the treatment plan may be shown in the user portal, as will be discussed in greater detail below. Additionally, once the treatment plan is approved by the doctor, the treatment plan may be automatically used for generating the aligners and automatically uploaded to the user portal.

In some embodiments, the doctor (e.g., the dentist, orthodontist, etc.) may approve of the treatment plan following the doctor seeing the user via a video conference or a video of the user. For instance, the doctor may "see" the user remotely prior to approving the treatment plan. In still other embodiments, the doctor may approve of the treatment plan without the video conference or the video of the user. In each of these embodiments, the doctor may approve of the treatment plan for the user without having to physically see the user in person. Accordingly, the user may not be inconvenienced with a trip to a doctor's office, which may also save time for the user.

Where the user 104 does not authorize fast tracking the generation of the aligners, the user 104 may authorize the treatment plan once the treatment plan is sent to the user 104 via the user portal. Following authorization of the treatment plan, the aligners may be generated and sent to the user 104. Additionally, following authorization of the treatment plan, the user 104 may then be prompted to pay for the aligners (or sign up for a payment plan).

In some embodiments, the treatment plan may be generated by a dental professional using a computing system at a treatment plan site. The treatment plan site may be separate from the intraoral scan sites, the fabrication site, etc. In other embodiments, the treatment plan site may be the same as the intraoral scan site and/or the fabrication site. Accordingly, two or more of these sites may be consolidated into one site.

The treatment plan may be generated by manipulating individual teeth in the three-dimensional representation of the user's mouth. For instance, the dental professional may manipulate one or more teeth of the user's mouth (as represented in the three-dimensional data) from a starting position (at the time of the intraoral scan) to an ending position (following treatment). Following the teeth being moved to the ending position, the treatment plan may automatically be generated (e.g., by a computer or computing system) in accordance with a set of rules. The set of rules may include rules which constrict an amount of movement of a single tooth between two sequential aligners (for instance, 3.00 mm). Following the treatment plan being generated, various models (e.g., positive molds of the user's dentition) may be generated which correspond to the position of the teeth at various intervals between the starting and ending position. The aligners may then be generated by thermoforming a polymer material to each of the various models (with a first aligner corresponding to the starting position of the user's teeth in the user's dentition, the second [and subsequent] aligner corresponding to an intermediate position[s], and the final aligner corresponding to the final position of the user's teeth in the user's dentition).

Following generation of the aligners, all aligners associated with the treatment plan may be sent to the user 104. In some implementations, the aligners may be generated and sent to the user 104 in packaging similar to the packaging described in U.S. Patent Application Ser. No. 62/522,847, filed on Jun. 21, 2017, titled "DENTAL IMPRESSION KITS AND METHODS THEREFOR," U.S. patent application Ser. No. 15/725,430, filed on Oct. 5, 2017 and having the same title, and U.S. Patent Application Ser. No. 62/648,229, filed on Mar. 26, 2018 and having the same title, each of which are incorporated by reference in their entirety as noted herein.

Post-Appointment

Following the user 104 having their intraoral scan administered at the scan shop 106, the user 104 may receive one or more messages generated via the message generator 136. Accordingly, in some embodiments, the message generator 136 can include instructions for generating and communicating one or more messages to the user 104 following the user's 104 appointment.

In some implementations, the message generator 136 can include instructions to generate a message including various surveys and/or questionnaires. These surveys may be used for evaluating the user's 104 experience at the intraoral scanning site 106. In some implementations, the surveys may solicit the user 104 for a review on a customer review website such as Yelp®, Google®, etc. Additionally, where the user 104 receives a whitening kit at their appointment, the message generated via the message generator 136 may include whitening tips for the user 104. In each of these implementations, the messages generated via the message generator 136 may be used as feedback for subsequent user's appointments, and to enhance the experience for the user 104.

In some implementations, the message generator 136 can include instructions for generating various messages specifically when a user 104 does not attend their appointment. For instance, when the user file 134 indicates the user 104 did not show up for their appointment, the message generator 136 can include instructions for automatically generating a message including a survey for evaluating reasons why the user 104 did not showed up for their appointment. The survey generated in these implementations may solicit the user 104 to provide suggestions of what the intraoral scanning site 106 (or website) could do differently. The survey generated in these implementations may also solicit the user 104 to provide information as to how the user 104 would like to be contacted in the future (e.g., via phone call, text message, email, etc.). In some instances, the message generated via the message generator 136 may include an indication to the user 104 that the user 104 does not require an appointment for an intraoral scan and that the user can show up at an intraoral scanning site 106 any time during business hours (e.g., that walk-ins are welcome). In each of these implementations, the messages are provided to the user 104 when the messages may increase the likelihood of the user 104 scheduling or otherwise visiting the intraoral scanning site 104, and may assist in improvements to the overall experience for other users.

Additionally, where the user 104 misses their appointment, in some instances, the user 104 may be provided a free at-home impression kit (similar to those described in U.S. Patent Application Ser. No. 62/522,847 and U.S. patent application Ser. No. 15/725,430). The at-home impression kit may be sent to the user 104 via first class mail. For instance, when the user file 134 indicates the user 104 did not show up for the appointment, the message generator 136 can include instructions to automatically generate a message to the user 104 that indicates that an at-home impression kit will be sent at no charge to the user 104. Additionally, the message generator 136 can include instructions to generate a prompt that is transmitted to, for instance, a processing or shipping warehouse. The prompt may include an address or shipping label and instructions to send an at-home impression kit to the user 104 at the address.

User Portal

Figure 8:
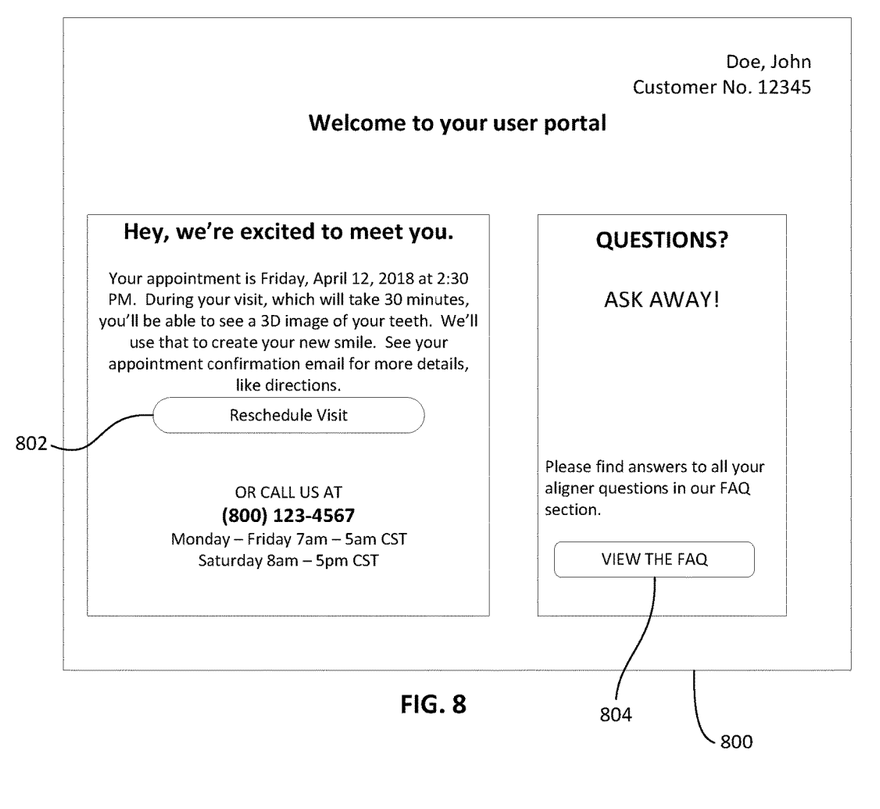
FIG. 8 is a user portal screen displayed to the user prior to the user's appointment according to an exemplary embodiment.

Referring now to FIG. 1 and FIG. 8, a user portal is generated for the user 104. Specifically shown in FIG. 8 is an example user portal 800 associated with the user 104. The example user portal 800 shown in FIG. 8 is generated prior to the user's 104 appointment. The appointment management system 100 may include a portal manager 140. The portal manager 140 may be or include instructions, that when executed by the processor 108, cause the processor 108 to generate/modify/change/manage one or more aspects of the user portal 800. As shown, the user portal 800 may include a brief overview of what to expect at the user's 104 appointment. The user portal 800 may include a button 802 to reschedule the user's 104 appointment. The button 802 may direct the user 104 to a page similar to reservation page 200. Additionally, the user portal 800 may include a button 804 to view a Frequently Asked Questions (FAQ) page providing answers to questions that the user 104 may have.

Figure 9:
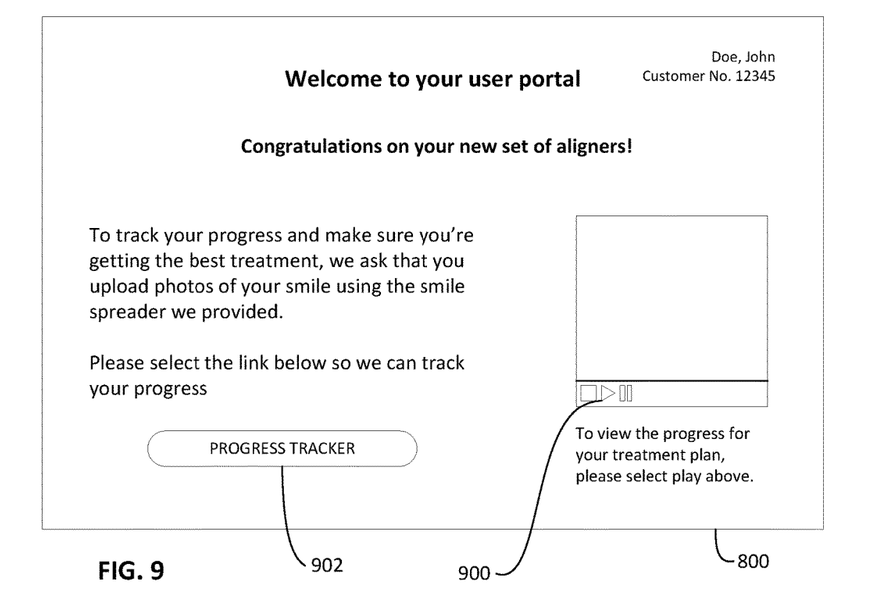
FIG. 9 is an example of a user portal screen displayed to the user following the user's appointment according to an exemplary embodiment.

Referring now to FIG. 1 and FIG. 9, the portal manager 140 may include instructions to modify the user portal 800 following the user's 104 appointment. For instance, as shown in FIG. 9, the user portal 800 is generated following the user's 104 appointment. The user portal 800 shown in FIG. 9 may include a visual representation (shown as a video) of the user's 104 treatment plan. The visual representation may show changes in the user's 104 smile as the user 104 progresses through various stages of the treatment plan. The visual representation may be a series of photos, a video, etc. The user 104 may be able to view the visual representation through selection of a button 900 (e.g., play button).

Additionally, the user 104 may be required (or requested) to provide progress information. As will be discussed in greater detail below, the progress information provided by the user 104 may be used for evaluating compliance and issuing a mid-course correction.

The user 104 may select a button 902 for providing progress information. The user 104 may be required to provide progress information at various stages along the treatment plan. For instance, the user 104 may be required to provide progress information at the outset of the treatment plan, as each aligner is used, following 90 days from the outset of the treatment plan, and/or other stages in the treatment plan. In some implementations, the appointment management system 100 may issue reminders to the user 104 for providing the progress information. For instance, the message generator 136 and/or portal manager 140 can include instructions to automatically generate one or more messages to communicate to the user 104 at various points throughout the treatment plan. As one example, when the aligners are received by the user 104 (e.g., as detected by a delivery notification), the delivery notification may be indicated in the user file 134. When the user file 134 indicates the delivery notification, the message generator 136 and/or portal manager 140 can include instructions to automatically generate one or more messages for the user 104 instructing the user 104 to provide initial progress data. When uploaded, the portal manager 140 can include instructions to store the initial progress data in the user file 134 as a baseline. The message generator 136 and/or portal manager 140 may include instructions to generate subsequent messages reminding the user 104 to upload progress data at various stages of the treatment plan, as described above. The message generator 136 and/or portal manager 140 can include instructions to identify a send date upon which the message corresponding to the initial progress data was communicated to the user 104. Additionally, the message generator 136 and/or portal manager 140 can include instructions to identify a current date. Based on a difference between the send date and the current date, the processor 108 may generate subsequent messages based on the instructions from the message generator 136 (and/or portal manager 140). Similarly, the message generator 136 and/or portal manager 140 can include instructions to generate messages directing the user 104 to change which aligners they are using (e.g., directing the user 104 to stop using a first set of aligns and to instead use a second set of aligners, directing the user 104 to stop using a third set of aligners and instead use the second set of aligners, to stop using the aligners altogether and to wait for new aligners to be sent to the user 104, etc.). Such messages may be generated similar to the messages for providing progress data.

Figure 10:
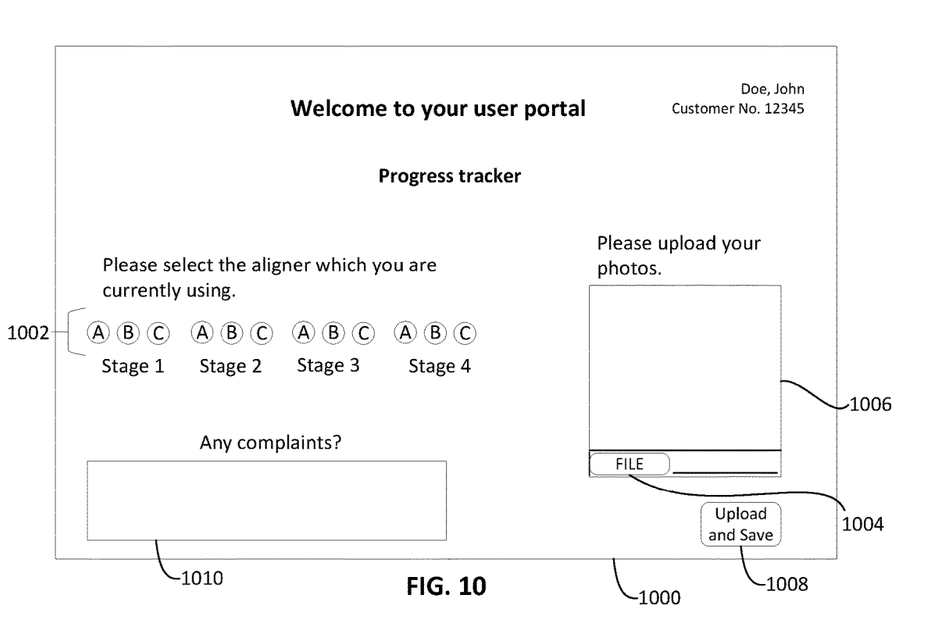
FIG. 10 is an example of a user portal screen displaying a progress tracker according to an exemplary embodiment.

Referring now to FIG. 1 and FIG. 10, upon selection of button 902, the portal manager 140 can include instructions to direct the user 104 to a progress tracker page 1000 within the user portal 800. Within the progress tracker page 1000, the user 104 is prompted to indicate which aligner the user 104 is currently using (e.g., through selection of a corresponding button 1002). Additionally, the user 104 is prompted to upload photos of the user's 104 smile. The user 104 may be instructed (e.g., either on the user portal 800, the progress tracker 1000, or separate instruction manual) on how to capture photos. For instance, the user 104 may be instructed to capture photos while using a smile spreader (e.g., a device positioned in the user's 104 mouth intended to push back the user's 104 lips and expose a greater area of the user's 104 teeth). The user 104 may be instructed to position the smile spreader in the user's 104 mouth and capture images at various angles. The user 104 may be instructed to capture an image of the user's 104 teeth head-on while biting down. The user 104 may be instructed to capture an image of the user's 104 lower jaw while opening the user's 104 mouth. The user 104 may be instructed to capture an image of the user's 104 upper jaw while opening the user's 104 mouth. The user 104 may be instructed to capture additional/alternative images of the user's 104 teeth. Each of these images may be uploaded by the user 104 using button 1004. Upon selection of button 1004, the user 104 may be prompted to search for and locate the image to upload. The image may be previewed (e.g., in display box 1006) once the user 104 locates the file. The user 104 may then select an upload button 1008 to upload the images to the user portal 800. When the images are uploaded, the portal manager 140 can include instructions to automatically add these images to the user file 134.

The user 104 may provide comments regarding the progress or fit of the aligners in comments box 1010. For instance, the user 104 may indicate that the user 104 is not satisfied with the progress of realigning the user's 104 teeth or how the user's 104 smile looks. As another example, the user 104 may indicate that the aligners do not fit or are uncomfortable. Each of these indications may indicate that the user 104 may require a mid-course correction. As used herein, a mid-course correction is defined as a new treatment plan developed for the user 104 following an indication that the current treatment plan is no longer desirable for the user 104. Accordingly, the user 104 receives a new intraoral scan, a new set of aligners, etc. In this regard, no cross-reference is made between the first treatment plan and the second treatment plan. However, in some implementations, the mid-course correction comprises receipt of at least one new set of aligners, which may be created for the user 104 following new intraoral scan or new impressions to be made of the user's 104 teeth. In some implementations, the mid-course correction may be free to the user 104. For instance, as discussed below, the mid-course correction may be free following a compliance check indicating that the user 104 is correctly following the treatment plan.

The compliance check may be a review of the progress data provided by the user (e.g., via progress tracker 1000). In some implementations, following the user 104 uploading any comments via comments box 1010, the portal manager 140 may include instructions to automatically flag the user file 134 and communicate the file to a professional terminal 142. The professional terminal 142 may be a computer associated with one or more professionals (e.g., doctors, dentists, orthodontists, etc.). The professional terminal 142 may display the user file 134 including the images uploaded by the user 104 and the current aligner which is being used by the user 104. The user file 134 may be evaluated by the professionals to determine whether the user 104 is progressing according to the treatment plan, whether the user 104 is following the treatment plan as instructed, etc. Where the user 104 is not following the treatment plan as instructed, the user file 134 may be flagged as not being in compliance. Where the user 104 is following the treatment plan but is not progressing according to the treatment plan, portal manager 140 may flag the user file 134 for a mid-course correction. Where the user file 134 is flagged as not being in compliance, the user 104 may be required to pay for the mid-course correction. However, where the user 104 is following the treatment plan, the mid-course correction may be offered to the user 104 for free.

In some implementations, when the user 104 is following the treatment plan as instructed and progresses through the treatment plan, the message generator 136 and/or portal manager 140 may include instructions to automatically generate a message (and corresponding flag in the user file 134) indicating that the user 104 is eligible for a free dental check-up and cleaning at a dental clinic or associated dental office.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media may be any available media that may be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision step.

What is claimed is:

1. A method comprising: determining, by an appointment management system, a condition that an appointment to conduct an intraoral scan at an intraoral scanning site has been missed by a user; automatically generating, by the appointment management system, a message to the user based on the condition that indicates that an at-home impression kit will be sent to the user; sending, by the appointment management system, the automatically generated message to the user; and sending the at-home impression kit to the user.

2. The method of claim 1 further comprising: automatically generating, by the appointment management system, a prompt for one of a processing or shipping warehouse; and transmitting the prompt to the one of the processing or shipping warehouse.

3. The method of claim 2, wherein the prompt comprises an address of the user and instructions to send the at-home impression kit to the address.

4. The method of claim 2, wherein the prompt comprises a shipping label associated with an address of the user, and wherein the prompt further comprises instructions to mail the at-home impression kit using the shipping label.

5. The method of claim 1, wherein the message to the user indicates that the at-home impression kit will be sent at no charge to the user.

6. The method of claim 1, further comprising sending the at-home impression kit to the user via first class mail.

7. The method of claim 1, further comprising receiving the at-home impression kit.

8. The method of claim 7, further comprising, determining, by the appointment management system, that the received at-home impression kit is complete.

9. The method of claim 7, further comprising, determining, by the appointment management system, that the impressions in the received at-home impression kit are incomplete.

10. The method of claim 9, further comprising, determining the impressions are incomplete in the received at-home impression kit by reviewing the impressions and determining their suitability for manufacturing dental aligners.

11. The method of claim 9, further comprising, determining, using a scan of the impressions, that the impressions are incomplete in the received at-home impression kit by reviewing the scan of the impressions and determining their suitability for manufacturing dental aligners.

12. A system comprising: an appointment management system configured to: determine a condition that an appointment to conduct an intraoral scan at an intraoral scanning site has been missed by a user; automatically generate a message to the user based on the condition that indicates that an at-home impression kit will be sent to the user; send the automatically generated message to the user; and send the at-home impression kit to the user.

13. The system of claim 12, the appointment management system further configured to: automatically generate a prompt for one of a processing or shipping warehouse; and transmit the prompt to the one of the processing or shipping warehouse.

14. The system of claim 13, wherein the prompt comprises an address of the user and instructions to send the at-home impression kit to the address.

15. The system of claim 13, wherein the prompt comprises a shipping label associated with an address of the user, and wherein the prompt further comprises instructions to mail the at-home impression kit using the shipping label.

16. The system of claim 12, wherein the message to the user indicates that the at-home impression kit will be sent at no charge to the user.

17. The system of claim 12, wherein the at-home impression kit is received from the user.

18. The system of claim 17, the appointment management system further configured to determine that the received at-home impression kit is one of complete or incomplete.

19. A method comprising: determining, by an appointment management system, a condition that an appointment to conduct an intraoral scan at an intraoral scanning site has been missed by a user; automatically generating, by the appointment management system, a message to the user based on the condition that indicates that an at-home impression kit will be sent to the user; sending, by the appointment management system, the automatically generated message to the user; automatically generating, by the appointment management system, a prompt for one of a processing or shipping warehouse, wherein the prompt comprises an address of the user and instructions to send the at-home impression kit to the address; transmitting the prompt to the one of the processing or shipping warehouse; sending the at-home impression kit to the user; receiving the at-home impression kit from the user; and producing, at a fabrication site, a plurality of aligners based on the received at-home impression kit, the plurality of aligners specific to the user and being configured to reposition one or more teeth of the user in accordance with a treatment plan.

\* \* \* \* \*